United States Patent

Gerstenberg et al.

(10) Patent No.: US 8,074,519 B2
(45) Date of Patent: Dec. 13, 2011

(54) METHOD AND APPARATUS FOR MONITORING A SYSTEM

(75) Inventors: Frank Gerstenberg, Berlin (DE); Georg Kinnemann, Bestensee (DE)

(73) Assignee: Siemens Aktiengesellschaft, Munich (DE)

( * ) Notice: Subject to any disclaimer, the term of this patent is extended or adjusted under 35 U.S.C. 154(b) by 381 days.

(21) Appl. No.: 12/467,325

(22) Filed: May 18, 2009

(65) Prior Publication Data

US 2009/0282922 A1   Nov. 19, 2009

(30) Foreign Application Priority Data

May 16, 2008 (DE) .......................... 10 2008 023 863

(51) Int. Cl.
*G01N 29/04* (2006.01)

(52) U.S. Cl. ................ 73/606; 73/598; 73/600

(58) Field of Classification Search ........................ None
See application file for complete search history.

(56) References Cited

U.S. PATENT DOCUMENTS

| | | | |
|---|---|---|---|
| 4,012,951 A * | 3/1977 | Kessler | 73/606 |
| 4,472,971 A * | 9/1984 | Marini et al. | 73/587 |
| 4,621,263 A | 11/1986 | Takenaka et al. | |
| 2008/0034869 A1 * | 2/2008 | Heinz et al. | 73/572 |
| 2009/0274006 A1 * | 11/2009 | Yockney | 367/138 |

FOREIGN PATENT DOCUMENTS

| | | |
|---|---|---|
| DE | 10304215 A1 | 8/2004 |
| WO | 2004017038 A1 | 2/2004 |

* cited by examiner

*Primary Examiner* — Andre Allen
(74) *Attorney, Agent, or Firm* — Laurence A. Greenberg; Werner H. Stemer; Ralph E. Locher

(57) ABSTRACT

A method for monitoring a system, in which a plurality of acoustic images are recorded and compared at defined intervals of time over a period of time extending several weeks. A large system can be monitored reliably and with little complexity if the acoustic images each contain a plurality of acoustic image areas which are arranged in a spatially different manner, and, between respective recordings of the image areas of an acoustic image, an acoustic sensor is aligned with an image area, which is to be recorded, of a next image area by being moved.

12 Claims, 2 Drawing Sheets

METHOD AND APPARATUS FOR MONITORING A SYSTEM

CROSS-REFERENCE TO RELATED APPLICATION

This application claims the priority, under 35 U.S.C. §119, of German application DE 10 2008 023 863.5, filed May 16, 2008; the prior application is herewith incorporated by reference in its entirety.

BACKGROUND OF THE INVENTION

Field of the Invention

The invention relates to a method for monitoring a system, in which a plurality of acoustic images are recorded and compared at defined intervals of time over a period of time extending several weeks.

Operators of large machines or systems incur high costs on account of unforeseen damage to wearing parts, for example bearings, belts, etc. If the defective parts are changed only after the defect has openly come to light, this is associated with failure of the affected system during the intended operating time and thus with losses in the operational throughput. In order to avoid this, wearing parts can be changed regularly, optimum maintenance cycles being able to be defined only for uniform wear behavior. In practice, the wear behavior is not uniform, thus resulting in unnecessary changing of parts or failures despite regular maintenance.

It is known practice to obtain statements on the state of wear from acoustic signals. International patent disclosure WO 04/017038 A1 presents a method in which a system is monitored with the aid of a portable directional microphone. Malfunctions within the system can be visualized by diagnosing the noise emitted by the running system in order to facilitate diagnosis for system maintenance. For this purpose, the directional microphone is aimed at the defective system and the frequency spectrum of the noise of the defective system is compared with a previously recorded frequency spectrum of the system without a defect. The type and location of the defect can be inferred using corresponding evaluations.

SUMMARY OF THE INVENTION

It is accordingly an object of the invention to provide a method and an apparatus for monitoring a system that overcome the above-mentioned disadvantages of the prior art devices and methods of this general type, which method can also be used to monitor a large system with simple measures.

With the foregoing and other objects in view there is provided, in accordance with the invention, a method for monitoring a system. The method includes recording and comparing a plurality of acoustic images at defined intervals of time over a period of time extending several weeks. The acoustic images each contain a plurality of acoustic image areas which are disposed in a spatially different manner, and, between respective recordings of the acoustic image areas of an acoustic image, an acoustic sensor is aligned with an image section, which is to be recorded, of a next image area by being moved.

The object is achieved by a method of the type mentioned at the outset, in which, according to the invention, the acoustic images each contain a plurality of acoustic image areas which are arranged in a spatially different manner, and, between respective recordings of the image areas of an acoustic image, an acoustic sensor is aligned with the image section, which is to be recorded, of the next image area by being moved. In particular, a large system with a multiplicity of system components can be monitored in this manner in an economically favorable and nevertheless reliable way using only a single acoustic sensor.

The system monitoring may be wear monitoring and/or defect monitoring. The method is particularly suitable for monitoring a system having a relatively large number of identical or similar functional units. Such a system is, for example, a mail sorting system which may have a large number of identical compartments, for example up to 1,000 compartments. In such a system, the wear on individual functional units progresses over a relatively long period of time, with the result that there is sufficient time for monitoring wear with measurements and evaluations. The spectra obtained from frequency analysis and/or amplitude distribution, for example, change over the course of time as a result of the wear on the functional units. Comparing these spectra with empirical values or spectra for a new system or a new functional unit can be used to determine a degree of wear on the individual functional units, with the result that decisions can be derived for service.

As a result of the automatable method according to the invention, there is no need to use a plurality of separate acoustic sensors in a large system having a large number of functional units. The method can thereby be carried out in a favorable manner and can remain in the background—as far as the apparatus complexity is concerned—such that the performance of the tasks of the systems is not impaired.

When carrying out the method according to the invention, it is sufficient to use only one single acoustic sensor to record all acoustic images. The acoustic sensor may be set up at a suitable distance from the system to be monitored and may be aimed at the system. The acoustic image containing acoustic data which are relevant to diagnosis—and possibly also further data—can now be obtained by a scanning movement of the acoustic sensor, the acoustic sensor recording image area by image area. The image areas may be arranged in a predetermined manner with respect to one another, with the result that the next orientation of the movement of the acoustic sensor between the recordings of the image areas may likewise be predetermined. This makes it possible to scan a plurality of signal sources, in particular identical or similar signal sources, in succession.

In order to determine wear or a defect, the acoustic images are advantageously recorded in an identical manner in order to achieve good comparability. The images can then be compared with one another. For example, a recorded image is compared with a previously recorded image, thus making it possible to determine the progress of wear or a defect from a change in the acoustic data. It is also possible to compare the recorded acoustic image with reference data which can be obtained, for example, from a first recorded image of a new system or can be concomitantly provided with the system or functional units. Images or image areas can be compared by comparing acoustic parameters.

The acoustic images are spatially assigned acoustic characteristics which may be composed of the acoustic image areas. They are expediently recorded in a predetermined rhythm, for example daily or weekly, in order to be able to respectively currently determine current progress of wear or a state of wear. The acoustic images can be compared with one another or with reference data by comparing an entire image with a previously recorded entire image or by comparing only a section of the acoustic image with an expediently identical section of an earlier image or corresponding reference data. An image area may be understood as meaning an assignment of noise data to spatial coordinates, an image area being able to be a point image, a line image, a two-dimensional image or even a 3-dimensional image.

The acoustic sensor can be moved by moving the inherent acoustic sensor element or an element of the sensor that guides sound waves to the sensor element.

The movement can be carried out in a particularly simple manner and with little outlay in terms of apparatus if the acoustic sensor is pivoted in order to be aligned with the next image section. The sensor may remain translationally at one location and may be pivoted in one dimension, for example, by a rotary drive in order to carry out a scanning movement in one line, for example. A rotary drive which allows pivoting in two dimensions is also conceivable, with the result that a plurality of lines can be scanned, for example.

The acoustic sensor may be intended to record airborne acoustic data, the sensor being aligned, during its movement, with a spatial area from which a new acoustic image area is intended to be recorded. A movable structure-borne sound sensor which acoustically measures an object via an acoustic bridge is likewise possible. The acoustic bridge, for example a steel spring, may be moved in a loop over the object or a plurality of objects and may make the acoustic recording in the process, the acoustic data being assigned, for example, to the coordinates of the respective support of the acoustic bridge and the acoustic image area thus being produced. Alternatively, the acoustic bridge may be set up at a location intended for it, for example, and may rest there while an acoustic measurement is being carried out. The bridge is then set up at another location and a new acoustic measurement is started.

In the case of a large, elongate system, such as a mail sorting system having a multiplicity of compartments, or in the case of a large rotary machine which is expediently acoustically imaged from a plurality of directions, the acoustic sensor may be translationally shifted by a transport apparatus in order to be aligned with the next image section. Particularly suitable for this is movement on a rail, in particular on a ceiling rail, from which the acoustic sensor can be suspended and can be moved with little generation of noise. A combination of translational and rotational movement of the acoustic sensor is particularly advantageous, thr sensor being able to record, for example, a first number of acoustic image areas solely by being pivoted and recording a further number of image areas following a translational movement, for example along an elongate fan apparatus.

A high level of positioning accuracy when evaluating a degree of wear can be achieved if the acoustic sensor is a directional microphone for recording spatial image areas. The sound pressure data of the spatial image areas can be separated from one another to a good extent, with the result that adjacent noise does not distort an image area very much.

Another advantage of the method is that suitable programming makes it possible to generate not only acoustic images with a rectangular outline but also any desired outlines of the acoustic images. An acoustic image whose outline corresponds to the outline of the system or to that area of the system which contains the functional units to be monitored is expediently generated. It is thus possible to avoid unnecessary measurements in systems with an outline which is not rectangular. Parts of the system which are not relevant to the measurements need not be scanned either. In this case, the outline of the system may be seen from the point of view of the acoustic sensor.

In another advantageous embodiment of the invention, acoustic image areas are examined for a temporary influence. It may be the case that the image areas are distorted by temporary obstacles, for example an operator. Such images which have been distorted by a temporary influence should be evaluated differently to image areas without the temporary influence or should be excluded from an evaluation. A temporary influence may be detected by sudden rough deviations from earlier image areas of the same functional unit or of the same image section occurring in an image area. In this case, a plausibility check is advantageously carried out, which check examines a rough deviation in order to determine whether it stems from wear or even a defect, for example a material fracture, or from a fault which cannot be taken into account, for example acoustic shadowing.

In a system having a multiplicity of functional units, it may be the case that the functional units have been subjected to a different degree of wear. In order to adapt the wear analysis to the current wear, it is advantageous if a scanning rate of the image areas is different. Image areas which image system parts which need to be monitored to a greater extent since they have been subjected to a greater degree of wear, for example, are generated more often than image areas of other system parts. The scanning rate can be adapted, for example, to a risk of wear.

A different degree of wear on the individual functional units may arise in the case of a multiplicity of identical functional units in the system to be monitored. A greater degree of wear on a functional unit in comparison with other functional units can be detected if image areas of an acoustic image are compared with one another.

Another embodiment variant of the invention proposes that the acoustic sensor is fastened to a person, and image areas are recorded during activities performed by the person in order to operate the system. In order to record the image areas, the acoustic sensor may be brought very close to a functional unit to be monitored or may be inserted into the latter without disturbing the person at work. Image areas and data obtained from the latter may be stored in a memory worn by the person or may be transmitted wirelessly, for example via WLAN, to a central data processing unit, for example.

The recordings are advantageously synchronized on the basis of a characteristic of the person. As a result, a time which is suitable for a recording can be determined by a process unit which can control the recording. The characteristic may be a location or an activity of the person that is suitable for a recording. The location can be determined by use of appropriate sensors and the activity can be determined, for example, by effects of the activity which are detected.

The recording synchronization is expediently triggered by an input by the person, which thereby controls the recording of an image area. A particularly favorable time for recording one or more image areas may be selected.

The recording synchronization may be triggered by the person operating the system, for example by acknowledging an activity, for example the acknowledgement that a compartment of a mail sorting system has been emptied. As a result, a controlling process unit can detect that the person is now very close to a functional unit as a result of carrying out the operation and there is thus a suitable moment for a recording.

In a mail sorting system, an image area is advantageously recorded when the person empties a sorting compartment, in particular while the person is reaching into the sorting compartment. An acoustic sensor which is fastened, for example, to the person's sleeve can thus be directly inserted into a functional unit, with the result that a very good acoustic image area can be obtained.

The acoustic image area can be obtained during a period of time, only a temporal section of the entire image area, for example, being used to evaluate the wear monitoring or defect monitoring, for example only such a temporal section in which the acoustic sensor is inside a sorting compartment by virtue of an operator. The recording may have already started beforehand by virtue of the recording synchronization, with the result that a first part of the recording is not used for wear analysis.

The invention is also aimed at an apparatus for monitoring a system, the apparatus has an acoustic sensor and a process unit which is intended to control the recording of a plurality of acoustic images and the comparison of the images at defined intervals of time over a period of time extending several weeks.

According to the invention, it is proposed that the apparatus contain a movement device for moving the acoustic sensor, and that the acoustic images each contain a plurality of acoustic image areas which are arranged in a spatially different manner, and that the process unit is intended to control a movement of the acoustic sensor between respective recordings of the image areas of an acoustic image such that the acoustic sensor is aligned with the image section, which is to be recorded, of the next image area.

Other features which are considered as characteristic for the invention are set forth in the appended claims.

Although the invention is illustrated and described herein as embodied in a method and an apparatus for monitoring a system, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
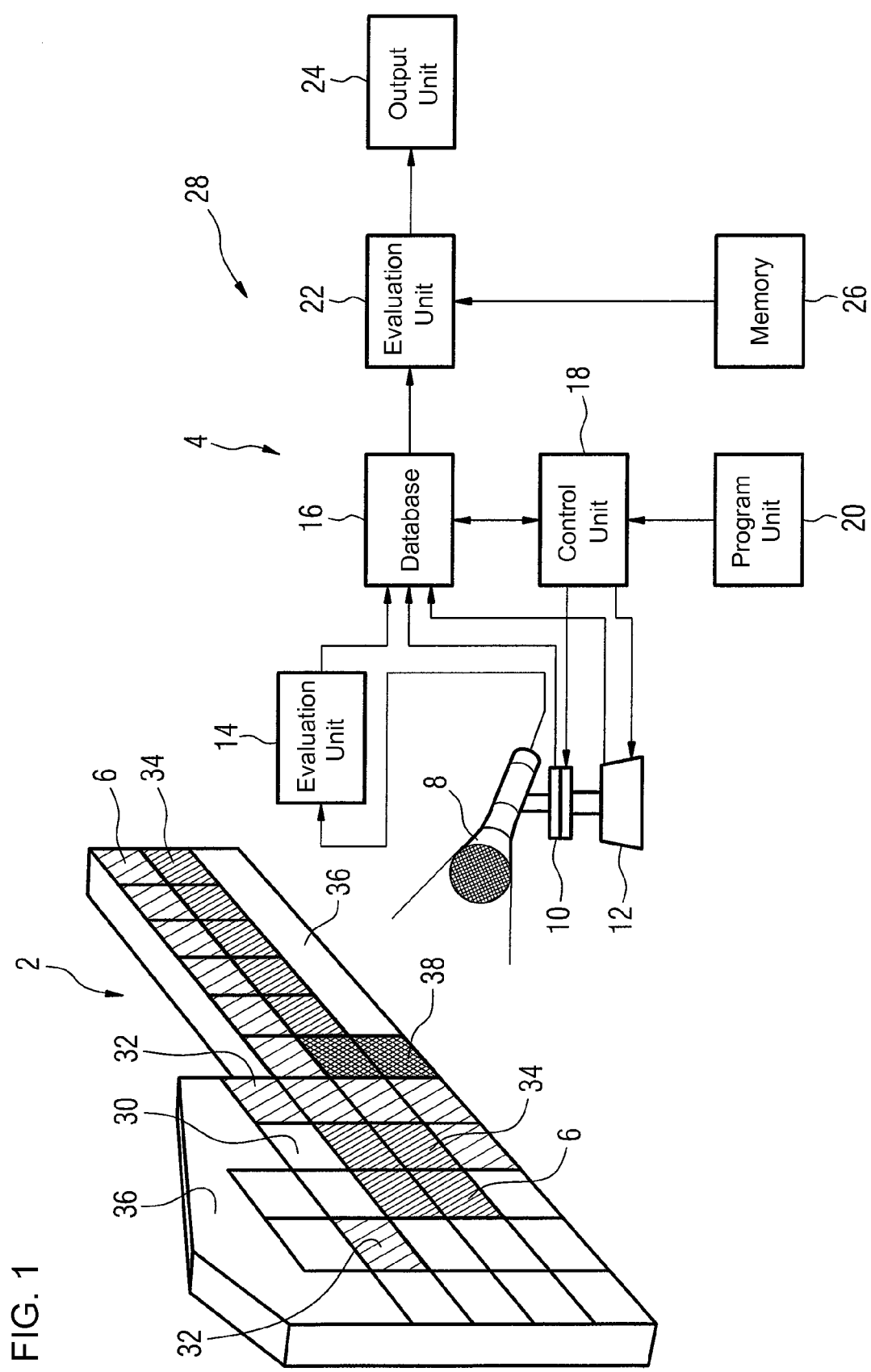
FIG. 1 is an illustration showing an apparatus for monitoring wear on a mail sorting system according to the invention.

Referring now to the figures of the drawing in detail and first, particularly, to FIG. 1 thereof, there is shown a diagrammatically simplified illustration of a system 2, for example a mail sorting system, which is monitored by a wear and/or defect monitoring apparatus 4 for wear on functional units 6 and the mechanical elements of the latter. The apparatus 4 which is likewise illustrated only diagrammatically in FIG. 1 includes an acoustic sensor 8 in the form of a directional microphone which is connected to a motor-driven rotating unit 10 having a vertical axis and to a motor-driven rotating unit 12 having a horizontal axis. The rotating units 10, 12 can pivot the acoustic sensor 8 in two dimensions about two shafts which are perpendicular to one another.

The apparatus 4 also contains an evaluation unit 14 for acoustic signals which are received by the acoustic sensor 8, a database 16 for acoustic parameters and rotary transducer signals for the two rotating units 10, 12, and a control unit 18 for the rotating units 10, 12, which control unit is connected to a program unit 20 for the rotatable units 10, 12. An evaluation unit 22 is used to evaluate the acoustic parameters determined and to forward the evaluation results to an output unit 24 for outputting data, for example information relating to repair and maintenance work, maintenance intervals, elements to be replaced, affected functional units 6 and the like. The evaluation unit 22 has access to a memory 26 for limit values of the acoustic parameters. The units 14 to 26 form a process unit 28 for controlling the monitoring of wear.

The drives of the two rotating units 10, 12 are controlled by the control unit 18 in such a manner that the entire system 2 can be scanned by moving the acoustic sensor 8 horizontally and vertically. The two drives simultaneously have rotary transducer outputs, the output signals from which are supplied to the database 16. The output of the acoustic sensor 8 is connected to the evaluation unit 14 which determines acoustic parameters of the system 2 which are then likewise supplied to the database 16. The database 16 thus stores a multiplicity of acoustic parameters of the system 2 to be monitored with their associated coordinates.

The evaluation unit 22 for the acoustic parameters determined obtains the limit values for the acoustic parameters from the memory 26 and compares them with the acoustic parameters determined and the values of the latter. If the evaluation unit 22 determines that the permissible limit values have been exceeded, it signals a necessary repair or maintenance measure via the output unit 24. The acoustic parameters may be amplitudes or frequencies or the distribution thereof and may generally be generated from the recorded acoustic signal by mathematical methods.

In order to monitor wear and/or defects of the system 2, the latter is subdivided into a number of areas 30, 32, 34, 36. The areas 30, 32, 34 may each be scanned by a single acoustic image area of the acoustic sensor 8. The areas 36 are not scanned by the acoustic sensor 8 since the elements or functional units arranged there are not intended to be monitored for wear. The acoustic image areas assigned to the areas 30, 32, 34 produce an acoustic image of the system 2 in their entirety or in subgroups. In this case, the areas 30, 32, 34 are arranged in rows—five rows in FIG. 1 by way of example—which can be scanned in succession by the acoustic sensor 8 with one image area per area 30, 32, 34.

In this case, the areas 30, 32, 34 are assigned to different scanning rates since the functional units 6 contained in them have been subject to a different degree of wear and can thus be assessed as more critical or less critical in terms of wear. The hatched areas 32 are checked at a first scanning rate, for example daily. The areas 34 with closer hatching are monitored at a higher scanning rate, that is to say in a more continuous manner in terms of time, for example every six seconds. The areas 30 which are not hatched are monitored at a lower scanning rate, for example weekly.

If evaluation of the acoustic data from the acoustic image areas reveals during recording and comparison that serious deviations from previous images occur in one or more image areas and these deviations are afflicted with attenuation or interfering noise which is not caused by wear, for example the pushing of a trolley past the system, those areas 38 which are cross-hatched in FIG. 1 and the acoustic image areas thereof may be excluded from the evaluation. The evaluation unit 22 can make a decision on this.

An acoustic image to be compared may contain one or more acoustic image areas. In a first variant, the acoustic images or acoustic data of the acoustic images are compared with a previously recorded acoustic image. This may be a reference image which was recorded when the system 2 was first operated or was new or which stems from a state of the system 2 or the functional units of the latter which has been run in but is completely intact in the corresponding area 30, 32, 34. In this manner, an acoustic image which is afflicted with interference can be compared with an "intact" acoustic image. Comparison with acoustic parameters which are predefined ex works and may be contained in the memory 26 is likewise possible.

Comparison with a plurality of previous acoustic images is also possible in order to detect a change profile of a parameter, for example amplitudes of chosen frequencies. In addition, comparison of a plurality of image areas, which are recorded in real time, for example in succession, in identical areas 30, 32, 34 is expedient. If, for example, a plurality of areas 34 which accommodate identical functional units 6 are scanned in succession, these image areas which are recorded in real time can be compared with one another. Evaluation of the image areas may be aimed at detecting abnormalities of individual functional units 6 in comparison with other functional units 6 and thus detecting individual defective or greatly worn functional units 6 from operational functional units 6.

Instead of the acoustic sensor 8, there may be a structure-borne sound sensor which acoustically measures vibrations which are transmitted from the areas 30, 32, 34 to a sensor means of the sensor via an acoustic bridge. For this purpose, the sensor may be moved from area 30, 32, 34 to area 30, 32, 34, the measurement taking place during the movement or between movements. In the case of measurement in a loop, for example, the acoustic bridge travels over the areas 30, 32, 34 on a path which is intended for it and is specially prepared for this purpose, for example in that it is not varnished. Alternatively, each area 30, 32, 34 may have one or more—in particular prepared—locations at which the bridge is set up and rests there during a measurement. The sensor is accordingly movable and can move or pivot.

Figure 2:
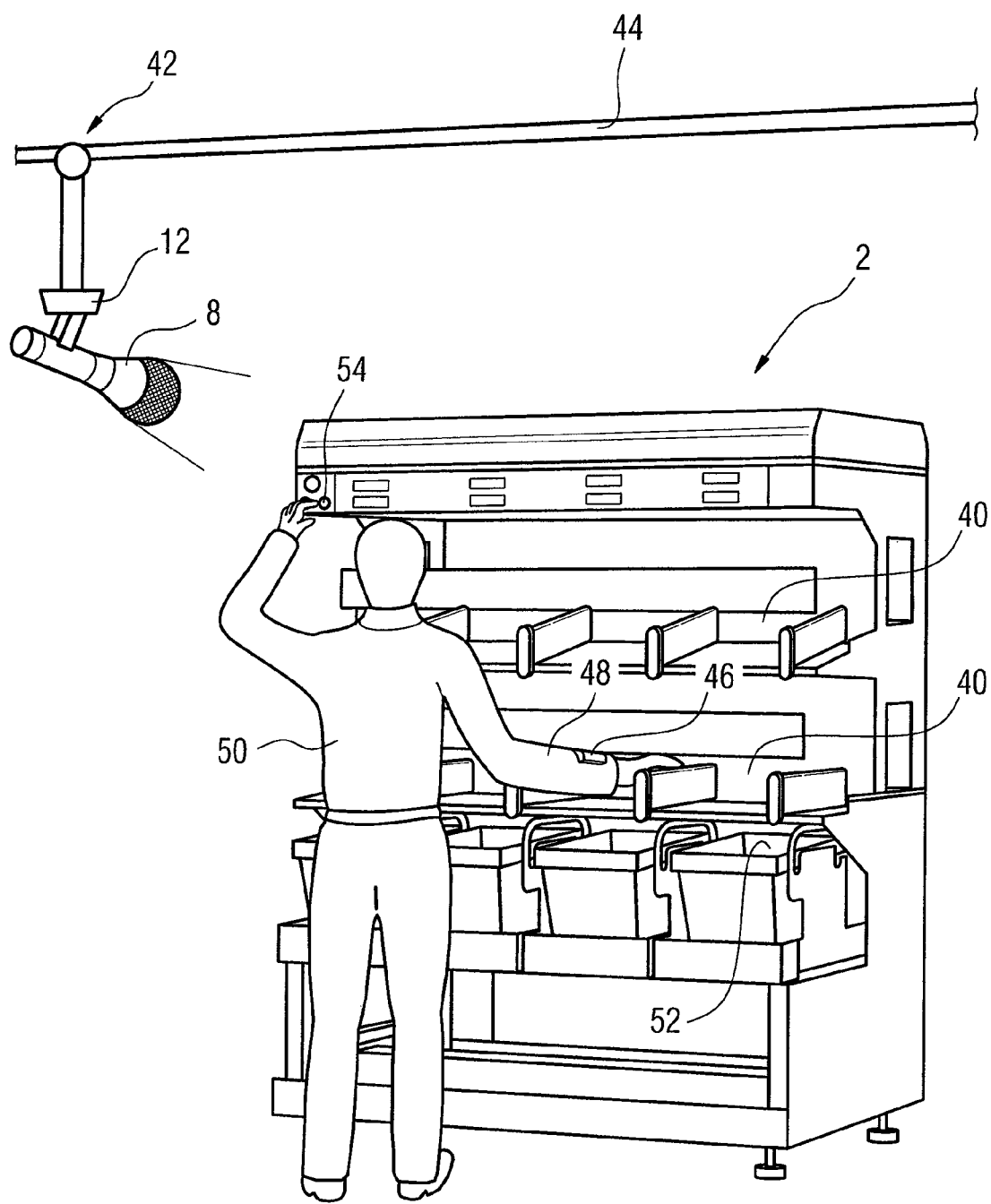
FIG. 2 is a diagrammatic, perspective view of a section of the mail sorting system and microphones of the apparatus, one of which is fastened to an operator of the mail sorting system.

Further possible ways of recording image areas are illustrated in FIG. 2. FIG. 2 shows a section of the system 2, namely a number of sorting compartments 40 in a sorting area of the system 2, which sorting area contains a total of 200 of such sorting compartments 40. Each sorting compartment 40 forms an area 34 which is recorded by an individual acoustic image area. Instead of the locally fastened acoustic sensor 8 or in addition to the latter, an acoustic sensor 8 is provided and can be pivoted by a rotating unit 12 and can be translationally shifted on a rail 44 by a transport apparatus 42. The acoustic sensor 8 can thus be moved along the 200 sorting compartments 40 and can be aligned with the individual areas 30, 32, 34 in this manner.

Alternatively or additionally again, an acoustic sensor 46 is provided. This sensor is fastened to a sleeve 48 of a person 50, for example an operator of the system 2. The operator empties the individual sorting compartments 40 if required and reaches into them for this purpose in order to remove items of mail which are stacked in them and to stack them in a container 52.

Before a sorting compartment 40 is emptied in this manner, the person 50 operates an acknowledgement button 54 by which the process unit 28 knows which sorting compartment 40 the person 50 is now beginning to empty. Operating the acknowledgement button 54 is a recording synchronization which is simultaneously an operation by the person 50, by which the process unit of the system 2 knows that the corresponding sorting compartment 40 is now being emptied and will then be available again for further stacking of items of mail.

Acoustic recording of the acoustic sensor 46 may begin after the acknowledgement button 54 has been operated and may be continued over a fixed period, for example. During this period, the person 50 reaches into the sorting compartment 40 and removes the items of mail stacked therein. In this case, the acoustic sensor 46 enters the interior of the sorting compartment 40 and can thus record the noise inside the sorting compartment 40 in a manner which is essentially undisturbed by ambient noise. From this relatively long recording, the process unit 28 may select a time range, for example in which particular noise is particularly loud or can be determined in an effective manner, and can restrict the acoustic image or the evaluation range of the latter to this smaller time range and can use this time range to evaluate the wear analysis.

The invention claimed is:

1. A method for monitoring a system, which comprises the steps of:
   recording and comparing a plurality of acoustic images at defined intervals of time over a period of time extending several weeks, the acoustic images each contain a plurality of acoustic image areas which are disposed in a spatially different manner, and, between respective recordings of the acoustic image areas of an acoustic image, an acoustic sensor is aligned with an image section, which is to be recorded, of a next image area by being moved.

2. The method according to claim 1, which further comprises pivoting the acoustic sensor in order to be aligned with the next image area.

3. The method according to claim 1, which further comprises providing the acoustic sensor as a directional microphone for recording spatial image areas.

4. The method according to claim 1, which further comprises matching an outline of the acoustic image to an outline of an area, which is to be monitored, of the system.

5. The method according to claim 1, which further comprises examining the acoustic image areas for a temporary influence.

6. The method according to claim 1, which further comprises setting a scanning rate of the acoustic image areas to be different.

7. The method according to claim 1, which further comprises comparing the acoustic image areas of the acoustic image with one another.

8. The method according to claim 1, which further comprises fastening the acoustic sensor to a person, and the acoustic image areas are recorded during activities performed by the person in order to operate the system.

9. The method according to claim 8, which further comprises synchronizing recordings on a basis of a characteristic of the person.

10. The method according to claim 9, which further comprises triggering a recording synchronization by an input from the person.

11. The method according to claim 9, which further comprises trigging a recording synchronization due to the person operating the system.

12. An apparatus for monitoring a system, the apparatus comprising:
    an acoustic sensor;
    a process unit for controlling a recording of a plurality of acoustic images and performing a comparison of the acoustic images at defined intervals of time over a period of time extending several weeks; and
    a movement device for moving said acoustic sensor, the acoustic images each containing a plurality of acoustic image areas which are disposed in a spatially different manner, and said process unit being intended to control a movement of said acoustic sensor between respective recordings of the acoustic image areas of an acoustic image such that the acoustic sensor is aligned with an image section, which is to be recorded, of a next image area.

* * * * *